(12) United States Patent
Bae et al.

(10) Patent No.: US 11,154,530 B2
(45) Date of Patent: *Oct. 26, 2021

(54) PHARMACEUTICAL COMPOSITION FOR TREATING LIVER CANCER, COMPRISING TETRAARSENIC HEXOXIDE CRYSTALLINE POLYMORPH

(71) Applicant: CHEMAS CO., LTD., Seoul (KR)

(72) Inventors: Ill Ju Bae, Gangwon-do (KR); Zenglin Lian, Beijing (CN)

(73) Assignee: CHEMAS CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/466,243

(22) PCT Filed: Dec. 4, 2017

(86) PCT No.: PCT/KR2017/014083
§ 371 (c)(1),
(2) Date: Jun. 3, 2019

(87) PCT Pub. No.: WO2018/105973
PCT Pub. Date: Jun. 14, 2018

(65) Prior Publication Data
US 2020/0069635 A1 Mar. 5, 2020

(30) Foreign Application Priority Data
Dec. 5, 2016 (KR) .................. 10-2016-0164595

(51) Int. Cl.
*A61K 31/285* (2006.01)
*A61K 33/36* (2006.01)
*C01G 28/00* (2006.01)

(52) U.S. Cl.
CPC ............ *A61K 31/285* (2013.01); *A61K 33/36* (2013.01); *C01G 28/008* (2013.01); *C01P 2002/60* (2013.01); *C01P 2002/72* (2013.01); *C01P 2002/88* (2013.01)

(58) Field of Classification Search
CPC .................................................. A61K 31/285
USPC ...................................................... 514/504
See application file for complete search history.

(56) References Cited

U.S. PATENT DOCUMENTS

| 10,493,100 | B2 * | 12/2019 | Bae | ............ A61K 31/285 |
| 10,525,079 | B2 * | 1/2020 | Bae | ............ A61K 31/285 |
| 2002/0028253 | A1 | 3/2002 | Bae et al. | |
| 2004/0018246 | A1 | 1/2004 | Bae et al. | |
| 2004/0213737 | A1 | 10/2004 | Huang et al. | |
| 2008/0193560 | A1 | 8/2008 | Hwang et al. | |

FOREIGN PATENT DOCUMENTS

| JP | H11-322616 | A | 11/1999 |
| KR | 10-0272835 | B1 | 11/2000 |
| KR | 10-2002-0095835 | A | 12/2002 |
| KR | 10-2010-0054210 | A | 5/2010 |
| WO | 2002/102814 | A1 | 12/2002 |
| WO | 2016/123603 | A2 | 8/2016 |
| WO | 2018093215 | A1 | 5/2018 |

OTHER PUBLICATIONS

Gilliam et al., "Raman spectroscopy of arsenolite: crystalline cubic AS4O6", Journal of Solid State Chemistry, vol. 173, No. 1, pp. 54-58 (2003).*
Generalic, Eni. "Face-centered cubic lattice." Croatian-English Chemistry Dictionary & Glossary, Oct. 20, 2018. (https://glossay.periodni.com/glossary.php?en=face-centered+cubic+lattice). (2018).*
International Search report issued for International Application No. PCT/KR2017/014083 dated Feb. 22, 2018, 6 pages.
Lee, Gwan Hui, "Studies on the Anticancer Activity of Arsenichexoxide(As4O6)" Korea Science and Engineering Foundation Targeted Basic Research Business, Jun. 2003, Grant No. 1350004221 (50 pages).
Search Report issued in the corresponding European Patent Application No. 17878050.8 dated May 25, 2020, 10 pages.
Office Action issued in the corresponding Canadian Patent Application No. 3044519 dated Jul. 2, 2020, 4 pages.
Lin Jiang et al., "As2O3 induces apoptosis in human hepatocellular carcinoma HepG2 cells through a ROS-mediated mitochondrial pathway and activation of caspases" Int J Clin Exp Med. 2015; 8(2): 2190-2196.
Anonymous: "Arsenolite R050383—RRUFF Data base: Raman, X-ray, Infrared, and Chemistry", RRUFF database, 2020, Retrieved from the Internet: <URL: https://rruff.info/Arsonolite/R050383> [Retreived on Apr. 23, 2020], 3 pages.
Cameron F. Holder et al., "Tutorial on Powder X-ray Diffraction for Characterizing Nanoscale Materials", ACS Nano, (2019) col. 13, No. 7, pp. 7359-7365.
Zdenka Slejkovec et al., "Arsenic trioxide versus tetraarsenic oxide in biomedical research: misunderstandings and misinterpretations" Biometals, (2012), 25(1), 231-5.
Nadra Sadaf et al., "Arsenic trioxide induces apoptosis and inhibits the growth of human liver cancer cells", Life Sciences (2018) vol. 205, pp. 9-17.
Lee Son Sup et al., "Tetraarsenic hexoxide demonstrates anticancer activity at least in part through suppression of NF-κB activity in SW620 human colon cancer cells", Oncol Rep, (2015), 33 (6): 2940-2946.

(Continued)

*Primary Examiner* — Kevin E Weddington
(74) *Attorney, Agent, or Firm* — Rothwell, Figg, Ernst & Manbeck, P.C.

(57) ABSTRACT

The present invention relates to a pharmaceutical composition for preventing or treating liver cancer and a method for producing same, the composition comprising tetraarsenic hexoxide in which the content of tetraarsenic hexoxide crystalline polymorph a (As$_4$O$_6$-a) is 99% or more. The composition of the present invention exhibits an excellent cancer cell proliferation inhibition effect and thus can be useful as an anticancer drug.

5 Claims, 3 Drawing Sheets

(56) References Cited

OTHER PUBLICATIONS

Office Action issued for Singapore Patent Application No. 11201904698T dated Feb. 13, 2020, 5 pages.
Raade, G. et al. "Kaatialaite, a new ferric arsenate mineral from Finland" American Mineralogist, vol. 69, pp. 383-387, 1984.
Park, et al.; "Tetraarsenic oxide, a novel orally administrable angiogenesis inhibitor"; Int J Oncol.; Jun. 2003; 22 (6):1271-6.

\* cited by examiner

PHARMACEUTICAL COMPOSITION FOR TREATING LIVER CANCER, COMPRISING TETRAARSENIC HEXOXIDE CRYSTALLINE POLYMORPH

CROSS-REFERENCE TO RELATED APPLICATIONS

The application is a 35 U.S.C. § 371 National Phase Entry Application from PCT/KR2017/014083, filed on Dec. 4, 2017, which claims the benefit of Korean Patent Application No. 10-2016-0164595 filed on Dec. 5, 2016, the disclosures of which are incorporated herein in their entirety by reference.

TECHNICAL FIELD

The present invention relates to a pharmaceutical composition containing a crystalline polymorph of tetraarsenic hexoxide for prevention or treatment of liver cancer.

BACKGROUND ART

Cancer is characterized by uncontrolled cell growth, and such abnormal cell growth forms a mass of cells called a tumor, which penetrates into surrounding tissues, and, in severe cases, causes metastasis into other organs of the body. Academically, tumors are called neoplasia. Cancer affects all tissues and organs of the body at various prevalence rates.

Liver cancer occurs when abnormal cells grow out of control in the liver, and primary liver cancer is the fourth most common fatal cancer death worldwide (Bosch F. X., et al., Primary liver cancer: worldwide incidence and trends, Gastroenterology, 127(s), s15-s16, 2004). In Korea, liver cancer is the leading cause of death among 40s and 50s males, and 22.6 people die per 100,000 people per year from liver cancer (Annual report cause of death 2004, National Statistical Office, 2005). Hepatocellular carcinoma (HCC) is currently the third most common cancer in Korea, and the 5-year survival rate is 9.6%, and thus hepatocellular carcinoma has a very poor prognosis.

The best treatment for hepatocellular carcinoma is surgical excision and liver transplantation. The donors are difficult to find although liver transplantation shows the best survival rate to date, and the number of patients to receive surgery is limited to 20% although surgical liver excision leads to a long survival period. Meanwhile, non-surgical local cancer removal treatments have been applied to advanced hepatocellular carcinoma on which liver transplantation or hepatectomy cannot be performed, and the examples of the treatments are carotid artery embolization, radiofrequency ablation, ethanol injection, radiotherapy, and the like.

The reasons why guidelines for effective treatment options are difficult to determine for patients with hepatocellular carcinoma are that, first, most patients with hepatocellular carcinoma have hepatocirrhosis, and second, the efficacy of the treatment is difficult to prove since death due to hepatic insufficiency accounts for a considerable number of fatalities. Therefore, in order to completely cure hepatocellular carcinoma in the future, endeavors are needed to improve treatment responses and survival rates through the combined treatment in which existing therapies with proven effects and new therapies are variously employed.

Therefore, with respect to liver cancer treatment, there is a continuing need for the development of therapeutic agents having excellent anti-cancer effects.

The present inventors have already received patent rights of technical features wherein tetraarsenic hexoxide purified from natural arsenolite containing arsenic through separation and purification techniques showed cancer metastasis suppressing effects in animal experiments and had excellent anticancer treatment effects when administered to end-stage cancer patients with uterine cancer, bladder cancer, lung cancer, maxillary sinus cancer, kidney cancer, and the like (Korean Patent No. 272835, Novel use of natural chemical substance tetraarsenic hexoxide as novel antitumor drug and pharmaceutical composition thereof, Registered on 30 Aug. 2000).

The present inventors, as a result of continuous research on arsenic, revealed that tetraarsenic hexoxide having 99% or more of tetraarsenic hexoxide crystalline polymorph a can be produced by a novel preparation method, different from the method disclosed in the above registered patent, and a composition containing such tetraarsenic hexoxide has a remarkable effect on liver cancer prevention or treatment, and completed the present invention.

DETAILED DESCRIPTION OF THE INVENTION

Technical Problem

An aspect of the present invention is to provide a pharmaceutical composition containing a crystalline polymorph of tetraarsenic hexoxide ($As_4O_6$) as an active ingredient for prevention or treatment of liver cancer.

Another aspect of the present invention is to provide a method for preparing a pharmaceutical composition containing a crystalline polymorph of tetraarsenic hexoxide ($As_4O_6$) as an active ingredient for prevention or treatment of liver cancer.

Technical Solution

The present invention is directed to a pharmaceutical composition containing tetraarsenic hexoxide ($As_4O_6$) as an active ingredient for prevention or treatment of liver cancer, wherein the tetraarsenic hexoxide includes 99% or more of tetraarsenic hexoxide crystalline polymorph a ($As_4O_6$-a).

The tetraarsenic hexoxide of the composition may be prepared by: a first step of heating sodium chloride at 100~800° C., followed by cooling; a second step of placing arsenic trioxide ($As_2O_3$) on the sodium chloride, followed by heating from 100° C. to 1000° C. in an airtight state and then cooling; a third step of separating crystals crystallized in a filter bed collecting sublimated arsenic; and a fourth step of repeating the second and third steps four to ten times using the crystals obtained in the third step instead of the arsenic trioxide in the second step, thereby obtaining tetraarsenic hexoxide crystals.

The tetraarsenic hexoxide of the composition may include less than 1% of tetraarsenic hexoxide crystalline polymorph b ($As_4O_6$-b).

The tetraarsenic hexoxide may have a purity of 99.9% or more.

The $As_4O_6$-a and $As_4O_6$-b may have features (i) to (iii) below.

TABLE 1

| Category | Crystalline polymorph a (As$_4$O$_6$-a) | Crystalline polymorph b (As$_4$O$_6$-b) |
|---|---|---|
| (i) Cell parameters | a = b = c = 11.0734 Å<br>α = β = γ = 90°<br>V = 1357.82 Å$^3$ | a = b = c = 11.0600 Å<br>α = β = γ = 90°<br>V = 1352.90 Å$^3$ |
| (ii) As—O bond length | 1.786 Å | 2.011 Å |
| (iii) O—As—O bond angle | 98.36° | 109.47° |

Figure 1:
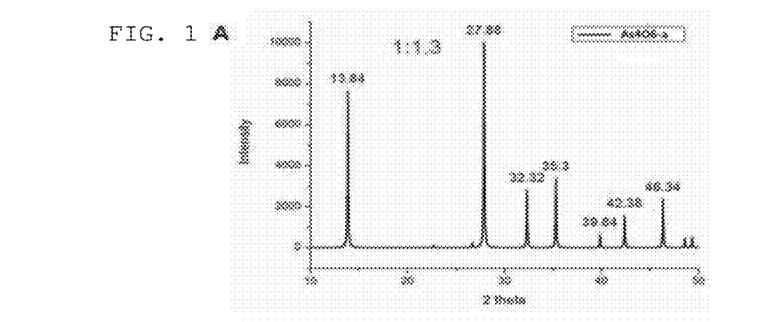
FIGS. 1A-B show X-ray powder diffraction spectrogram of $As_4O_6$-a and $As_4O_6$-b.

The As$_4$O$_6$-a has a crystal form, of which the X-ray powder diffraction spectrum obtained by using a light source wavelength of 1.5406 Å within a diffraction angle (2θ) of 10° to 50° at a rate of 1°/min (scan step of 0.02°) shows peaks at 2θ values of 13.84, 27.88, 32.32, 35.3, 39.84, 42.38, 46.34, 48.6, and 49.34 (see FIGS. 1A-B). In addition, the ratio of main peaks shown at 2θ values of 13.8 and 27.9 is 1:1.3.

The As$_4$O$_6$-b has a crystal form, of which the X-ray powder diffraction spectrum obtained by using a light source wavelength of 1.5406 Å within a diffraction angle (2θ) of 10° to 500 at a rate of 1°/min (scan step of 0.020) shows peaks at 2θ values of 13.86, 27.92, 32.36, 35.34, 39.9, 42.44, 46.4, 48.66, and 49.4 (see FIGS. 1A-B). In addition, the ratio of main peaks shown at 2θ values of 13.8 and 27.9 is 1:2.5.

Hereinafter, the present invention will be described in detail.

The present invention is directed to a pharmaceutical composition containing tetraarsenic hexoxide (As$_4$O$_6$) as an active ingredient for prevention or treatment of liver cancer, wherein the tetraarsenic hexoxide includes 99% or more of tetraarsenic hexoxide crystalline polymorph a (As$_4$O$_6$-a).

In accordance with another aspect of the present invention, there is provided a method for preparing a pharmaceutical composition containing a crystalline polymorph of tetraarsenic hexoxide (As$_4$O$_6$) as an active ingredient for prevention or treatment of liver cancer, the method including: a first step of heating sodium chloride at 100~800° C., followed by cooling; a second step of placing arsenic trioxide (As$_2$O$_3$) on the sodium chloride, followed by heating from 100° C. to 1000° C. in an airtight state and then cooling; a third step of separating crystals crystallized in a filter bed collecting sublimated arsenic; and a fourth step of repeating the second and third steps four to ten times using the crystals obtained in the third step instead of the arsenic trioxide in the second step, thereby obtaining tetraarsenic hexoxide crystals, wherein the tetraarsenic hexoxide crystals obtained in the fourth step include 99% or more of tetraarsenic hexoxide crystalline polymorph a (As$_4$O$_6$-a).

A synthesis reactor of a kaolin material and clamps capable of mounting filters thereon above the synthesis reactor are prepared. Then, sodium chloride is placed in the synthesis reactor, and heated and cooled. The reason why sodium chloride is used in the preparation method of the present invention is that when heating is carried out while arsenic trioxide is placed on the sodium chloride in the second step, heat is uniformly transferred to arsenic compounds, thereby helping the sublimation of the arsenic compounds. In order to remove impurities and moisture from such sodium chloride, the sodium chloride is heated at 100-800° C. for 2-6 hours in the first step. In the first step, the sodium chloride is cooled at room temperature for 3-10 hours after the heating.

Then, the second step is conducted by placing arsenic trioxide (As$_2$O$_3$) on the sodium chloride, followed by heating from 100° C. to 1000° C. in an airtight state and then cooling. Here, after the placing of arsenic trioxide, three to six filters (filter beds) capable of collecting sublimated arsenic are mounted on the clamps such that the intervals between the filters are 2-6 mm. The filters used herein preferably have a basic weight of 70-100 g/m$^2$, a thickness of 0.17-0.25 mm, a filtration speed of 22-30 s/100 ml, and a retention rate of 5-10 μm.

After the mounting of the filters, an airtight state was made, and then a bottom portion of the synthesis reactor is heated for 3-10 hours while the temperature is gradationally raised from 100° C. to 1000° C., so that the temperature of the center portion of the highest filter bed is maintained at 150±100° C., and tetraarsenic hexoxide is crystallized passing through the filter beds. Then, cooling is carried out at room temperature for 5 hours or longer, and preferably 5-10 hours.

Then, the third step is conducted by separating white crystals collected in the three to six spaced filter beds installed in a stacked type.

After a small amount of arsenic trioxide remaining on the sodium chloride in the synthesis reactor is removed, the collected white crystals are placed thereon, and then the second and third steps are repeated four to ten times in the same conditions, thereby finally obtaining tetraarsenic hexoxide crystals. As a result of checking the crystal structures obtained according to the preparation method of the present invention, it was verified that most of the crystals were As$_4$O$_6$-a, which accounted for 99% or more.

The pharmaceutical composition containing a crystalline polymorph of tetraarsenic hexoxide of the present invention can be favorably used in the prevention or treatment of liver cancer.

The pharmaceutical composition of the present invention may be formulated in the form of: an oral formulation, such as a powder, granules, a tablet, a capsule, a suspension, an emulsion, a syrup, or an aerosol; an externally applied preparation; a suppository; and a sterile injectable solution, according to usual methods, respectively. Examples of a carrier, an excipient, and a diluent that may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may be formulated into preparations by using a diluent or an excipient, such as a filler, an extender, a binder, a wetting agent, a disintegrant, or a surfactant. A solid preparation for oral administration includes a tablet, a pill, a powder, granules, a capsule, and the like. These solid preparations may be prepared by mixing the tetraarsenic hexoxide of the present invention with at least one excipient, for example, starch, calcium carbonate, sucrose or lactose, gelatin, or the like. Also, lubricants, such as magnesium stearate and talc, may be used in addition to simple excipients. A liquid preparation for oral administration corresponds to a suspension, a liquid for internal use, an emulsion, a syrup, and the like, and may include simple diluents that are frequently used, such as water and liquid paraffin, and several excipients, such as a wetting agent, a sweetener, an aromatic agent, and a preservative. A preparation for parenteral administration includes a sterile aqueous solution, a non-aqueous solvent, a suspension, an emulsion, a freeze-drying agent, and a suppository.

The non-aqueous solvent and the suspension may include propylene glycol, polyethylene glycol, vegetable oils such as olive oil, injectable esters such as ethylolate, and the like. A base material for the suppository may include Witepsol, Macrogol, Tween 61, cacao butter, laurin butter, glycerogelatin, and the like.

The dose of the pharmaceutical composition may vary depending on age, gender, and body weight of a subject to be treated, a particular disease or pathological condition to be treated, severity of a disease or pathological condition, route of administration, and determination of a prescriber. The determination of the dose based on these factors is within the level of a person skilled in the art, and the general dose is in the range of approximately 0.01-500 mg/kg/day. A more preferable dose is 0.1-100 mg/kg/day. The administration may be carried out once a day or several times in a divided dose a day. The above dose is not intended to restrict the scope of the present invention in any way.

The pharmaceutical composition may be administered to mammals, such as rats, domestic animals, and humans, via various routes. All manners of administration may be predicted, and for example, the administration may be carried out through oral, rectal, intravenous, intramuscular, subcutaneous, endometrial, intracerebroventricular injection.

Advantageous Effects

The pharmaceutical compositions for prevention or treatment of liver cancer of the present invention have excellent anticancer effects by containing tetraarsenic hexoxide including 99% or more of tetraarsenic hexoxide crystalline polymorph a.

MODE FOR CARRYING OUT THE INVENTION

Hereinafter, preferable examples of the present invention will be described in detail. However, the present invention is not limited to the examples described herein, and thus may be embodied into different forms. Rather, these examples are provided so that this disclosure will be thorough and complete, and will fully convey the scope of the invention to those skilled in the art.

Example 1: Preparation of Present Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m², a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters.

The collected white crystals were placed on the coarse salt inside the synthesis reactor, and the heating, cooling, and crystal collecting processes were again repeated four times, thereby finally obtaining 12.0 g of the crystals. As a result of checking the structure of the obtained arsenic compound crystals, it was confirmed that most of the crystals were $As_4O_6$-a while 99 wt % or more of $As_4O_6$-a and less than 1 wt % of $As_4O_6$-b were obtained.

It was confirmed that as for the differential scanning calorimetry (DSC) value at a temperature rise rate of 10° C./min, $As_4O_6$-a showed an endothermic peak (melting point) at 282.67° C. and $As_4O_6$-b showed an endothermic peak (melting point) at 286.77° C.

X-ray powder diffraction spectra of $As_4O_6$-a and $As_4O_6$-b are shown in FIGS. 1A-B, and diffraction data of $As_4O_6$-a and $As_4O_6$-b are shown in Table 2 below.

TABLE 2

| $As_4O_6$-a | | $As_4O_6$-b | |
|---|---|---|---|
| 2θ (°) | Diffraction intensity | 2θ (°) | Diffraction intensity |
| 13.84 | 7631.01 | 13.86 | 4012.09 |
| 27.88 | 10000 | 27.92 | 10000 |
| 32.32 | 2801.74 | 32.36 | 2130.23 |
| 35.3 | 3369.82 | 35.34 | 2511 |
| 39.84 | 623.242 | 39.9 | 447.422 |
| 42.38 | 1551.5 | 42.44 | 1431.86 |
| 46.34 | 2345.2 | 46.4 | 4159.8 |
| 48.6 | 447.69 | 48.66 | 564.995 |
| 49.34 | 502.761 | 49.4 | 375.571 |

As confirmed in FIGS. 1A-B and Table 2, the ratio of main peaks shown at 2θ values of 13.8 and 27.9 was 1:1.3 in $As_4O_6$-a, and the ratio of main peaks shown at 2θ values of 13.8 and 27.9 was 1:2.5 in $As_4O_6$-b. DSC analysis, structure determination, and X-ray diffraction analysis of the prepared compounds were carried out by the following methods.

(1) DSC Analysis

Using a DSC system (SDT Q600 V20.9 Build 20), 20.0 mg of a sample was analyzed while the temperature was raised to 310° C. at a temperature rise rate of 10° C./min with $N_2$ flowing out at 100 mL/min.

(2) X-Ray Crystallography

Single crystals of tetraarsenic hexoxide ($As_4O_6$, MW=395.6) were placed on a glass fiber and then an X-ray beam was applied thereto, to observe diffraction patterns on photographic films and the presence or absence of the organization of diffraction data, thereby determining space groups and cell parameters. Diffraction intensities were collected in the range of 10°<2θ<50°. The crystal structure of $As_4O_6$ was determined from the data by the Patterson method by using a structure determination program (SHELXTL program).

(3) X-Ray Diffractometry

A sample was prepared by pulverizing the obtained crystals into particles having a size of 10-30 μm (−325 mesh), filling a glass holder for X-ray diffraction analysis (20 mm×16 mm×1 mm) with the particles, compressing the particles by a glass slide or the like, and flattening the particles to allow a sample surface to be parallel with a holder surface. The X-ray diffraction spectrum of the crystals was drawn using Cu Kα$_1$ (1.54060 Å) of XRD within a diffraction angle (2θ) of 10° to 50° at a rate of 1°/min (scan step of 0.02°).

Comparative Example 1: Preparation of Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m$^2$, a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters. 48.5 g of crystals were collected from the filters. As a result of checking the crystal structure of the collected arsenic compounds, it was confirmed that $As_4O_6$-b accounted for 99 wt % or more.

Comparative Examples 2 to 4: Preparation of Tetraarsenic Hexoxide

Comparative Examples 2 and 3 were prepared by mixing Example 1 (composition having 99% or more of crystalline polymorph $As_4O_6$-a) and Comparative Example 1 (composition having 99% or more of crystalline polymorph $As_4O_6$-b) at 4:1 and 1:1, respectively.

Test Example 1: Test on Human Liver Cancer Cell Proliferation Inhibitory Effects (1) Materials and Cell Culture Fetal bovine serum (FBS) and cell culture medium were prepared (Hyclone), and dimethyl sulfoxide (DMSO) and 3-(4,5-dimethyl-thiazol-2yl)-2,5-diphenyltetrazolium bromide (MTT, Amresco LLC, USC) were prepared.

As human cancer cell lines, human liver cancer cells SMMC-7721 and HCCLM3 were obtained from the Shanghai Cell Bank of Chinese Academy of Sciences. The SMMC-7721 cells were incubated in RPMI-1640 medium supplemented with 10% FBS, 50 U/ml penicillin, and 50 μg/ml streptomycin and the HCCLM3 cells were incubated in Dulbecco's modified Eagle's medium (DMEM) supplemented with 10% FBS, 100 U/ml penicillin, and 100 μg/ml streptomycin in a humidified incubator with 5% $CO_2$ and 95% air. The media were exchanged every three days.

(2) Cell Proliferation Assay (MTT Assay)

The effects of Example 1 and Comparative Examples 1 to 3 on cell proliferation were assessed using MTT assay. MTT assay is based on the ability of viable cells against MTT to produce insoluble dark blue formazan products. After the cells were suspended in the medium by trypsin treatment and collected, the cells were dispensed at a density of $4 \times 10^3$ cells/well in a 96-well culture dish (Costar, Cambridge, Mass., USA). After 24 hours, the cells in the media containing 10% FBS were treated with Example 1 and Comparative Examples 1 to 3, at 0, 0.625, 1.25, 2.5, 5, 10, 20, 40, or 80 µM, and then incubated. Here, stock solutions obtained by dissolving Example 1 and Comparative Examples 1 to 3 at $5 \times 10^{-2}$ M in 1 M sodium hydroxide was used. For MTT assay for cell proliferation, supernatants were removed from the cells incubated for 48 hours, and 72 hours after the sample treatment, and 20 µl of 5 mg/ml MTT solution was added per well, and the cells were incubated at 37° C. for 4 hours to form formazan crystals. After the incubation, supernatants were again removed, followed by addition of 100 µl of DMSO to every well, and then mixing was carried out to completely dissolve dark blue crystals. All the crystals were completely dissolved by standing at room temperature for 15 minutes, and the absorbance was measured using a microplate reader at a wavelength of 570 nm ($A_{570nm}$).

(3) Statistical Analysis

The absorbance value of the control group treated without the sample was calculated as 100, and the absorbance value of the treatment group treated with the sample, compared with that of the control group, was calibrated, and the percentage of inhibition of cell proliferation was calculated according to the following equation.

Percentage (%) of inhibition of cell proliferation=
((mean absorbance of control group cells−mean absorbance of treatment group cells)/mean absorbance of control group cells)×100

All data were expressed as mean±standard error of the mean (mean±SEM). One-way analysis of variance (ANOVA) followed by Dunnett's post-test was used to perform multiple comparison. Statistical significance was defined as $p<0.05$, and each test was repeated three times.

(4) Results of Test Using SMMC-7721 Cells

Figure 2:
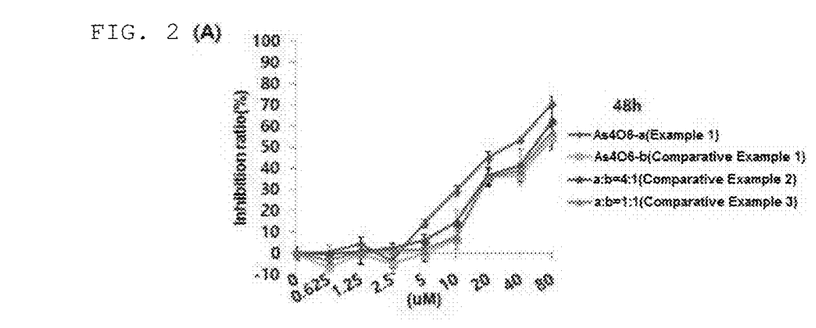
FIGS. 2A-B show graphs depicting the results of assessing cell proliferation inhibitory effects through MTT assay after SMMC-7721 cells were treated with Example 1 and Comparative Examples 1 to 3 and incubated for 48 hours (FIG. 2A) and 72 hours (FIG. 2B).

The human liver cancer cell line SMMC-7721 cells were treated with Example 1 and Comparative Examples 1 to 3, and incubated for 48 and 72 hours, followed by MTT assay. The results are shown in FIGS. 2A-B. It was confirmed that the percentages of inhibition of the liver cancer cell line SMMC-7721 cell proliferation were higher in the treatment with Example 1 and then the incubation for 48 hours (FIG. 2A) and 72 hours (FIG. 2B) compared with the treatment with Comparative Example 1. It was also confirmed that the percentage of inhibition of SMMC-7721 cell proliferation was higher in Example 1 than Comparative Example 2 or 3 in which Example 1 and Comparative Example 1 were mixed at 4:1 or 1:1.

(5) Results of Test Using HCCLM3 Cells

Figure 3:
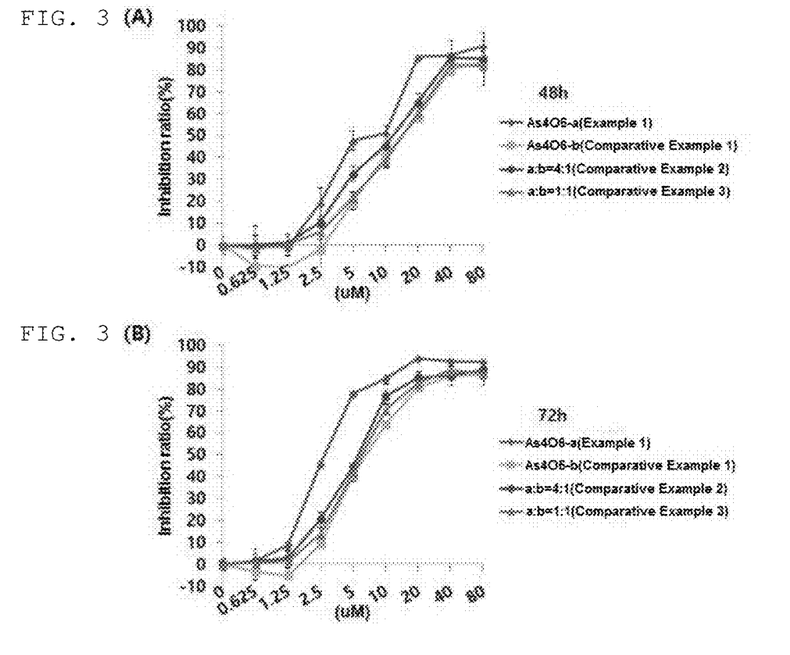
FIGS. 3A-B show graphs depicting the results of assessing cell proliferation inhibitory effects through MTT assay after HCCLM3 cells were treated with Example 1 and Comparative Examples 1 to 3 and incubated for 48 hours (FIG. 3A) and 72 hours (FIG. 3B).

The human liver cancer cell line HCCLM3 cells were treated with Example 1 and Comparative Examples 1 to 3, and incubated for 48 and 72 hours, followed by MTT assay. The results are shown in FIGS. 3A-B. It was confirmed that the percentages of inhibition of the liver cancer cell line HCCLM3 cell proliferation were higher in the treatment with Example 1 and then the incubation for 48 hours (FIG. 3A) and 72 hours (FIG. 3B) compared with the treatment with Comparative Example 1. It was also confirmed that the percentage of inhibition of HCCLM3 cell proliferation was higher in Example 1 than Comparative Example 2 or 3 in which Example 1 and Comparative Example 1 were mixed at 4:1 or 1:1.

Test Example 2: In Vivo Efficacy Test in Animal Models Transplanted with Human Liver Cancer Cell Line H22 Cells (1) Methods Human liver cancer cell line H22 cells (purchased from the Shanghai Cell Bank of Chinese Academy of Sciences) were incubated in RPMI-1640 medium supplemented with 10% FBS, 100 U/ml penicillin, and 100 µg/ml streptomycin in an incubator under conditions of 37° C., 5% $CO_2$, and 95% air. The medium was exchanged every three days.

Fifty 6-week-old ICR female and male mice, which were safe from specific pathogens and respiratory diseases and had a body weight of 18-20 g, were used as experimental animals. The mice were allowed free access to food and water, and were bred in a 12-hr light/12-hr dark cycle.

Out of the 50 mice, 10 mice were classified as the normal group, and the remaining 40 animals were subcutaneously inoculated with H22 cells at $1 \times 10^7$ cells per mouse, and bred for 7 days. On 7 days after the cell inoculation, the mice were randomly divided into 10 mice per group, and then test groups were designated as shown in Table 3 below, and respective corresponding samples were orally administered daily for 11 days. 5-Fluorouracil (5-FU), which is used as an anticancer drug, was treated for a positive control group.

TABLE 3

| Group | Treatment information | |
|---|---|---|
| | H22 cell inoculation | Reagent treatment |
| Normal control group | Untreated | Untreated |
| Cancer model group | Treated | Distilled water |
| Test Group 1 | Treated | Example 1 - 4.5 mg/kg |
| Test Group 2 | Treated | Example 1 - 2.25 mg/kg |
| Positive control group | Treated | 5-Fluorouracil - 20 mg/kg |

(2) Investigation of Cancer Growth Inhibition

After the administration of the drug for each group, cancer sizes were measured daily using a Vernier caliper, and cancer volumes were calculated using the equation $V=0.5 \times ab^2$ (a is the longest diameter of cancer and b is the shortest diameter of cancer). The results are shown in Table 4 and FIG. 4. In addition, the inhibition of cancer volume according to the number of days of administration was calculated by the following equation. The results are shown in Table 5 and FIG. 5.

Percentage of inhibition of cancer growth=(1−(sample treatment group/cancer model group))×100

TABLE 4

| | Cancer volume (mm³) according to number of days of administration | | | |
|---|---|---|---|---|
| Group | 5 days | 7 days | 9 days | 11 days |
| Cancer model group | 224.29 | 399.47 | 664.71 | 1812.69 |
| Positive control group | 165.62 | 212.78 | 318.07 | 661.97 |
| Test Group 1 | 168.09 | 238.22 | 388.85 | 880.55 |
| Test Group 2 | 216.75 | 302.66 | 388.56 | 987.61 |

TABLE 5

| Group | Percentage (%) of inhibition of cancer growth | | | |
|---|---|---|---|---|
| | 5 days | 7 days | 9 days | 11 days |
| Positive control group | 26.16 | 46.73 | 52.15 | 63.48 |
| Test Group 1 | 25.06 | 40.36 | 41.50 | 51.42 |
| Test Group 2 | 3.36 | 24.23 | 41.54 | 45.52 |

Figure 4:
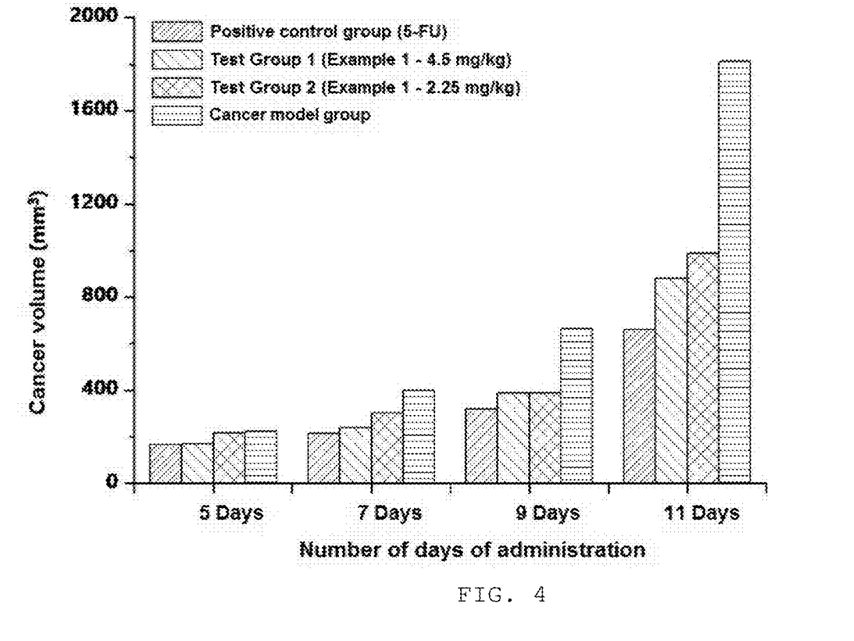
FIG. 4 is a graph showing the results of investigating the changes in cancer volume according to the treatment amount and treatment time of Example 1 when mice transplanted with the human hepatoma cell line H22 cells were treated with Example 1.

As can be seen from Table 4 above and FIG. 4, the cancer volumes were reduced according to the period of administration in Test Groups 1 and 2 administered with Example 1 compared with the cancer model group, and the cancer volumes were also reduced according to the amount of Example 1 administered.

Figure 5:
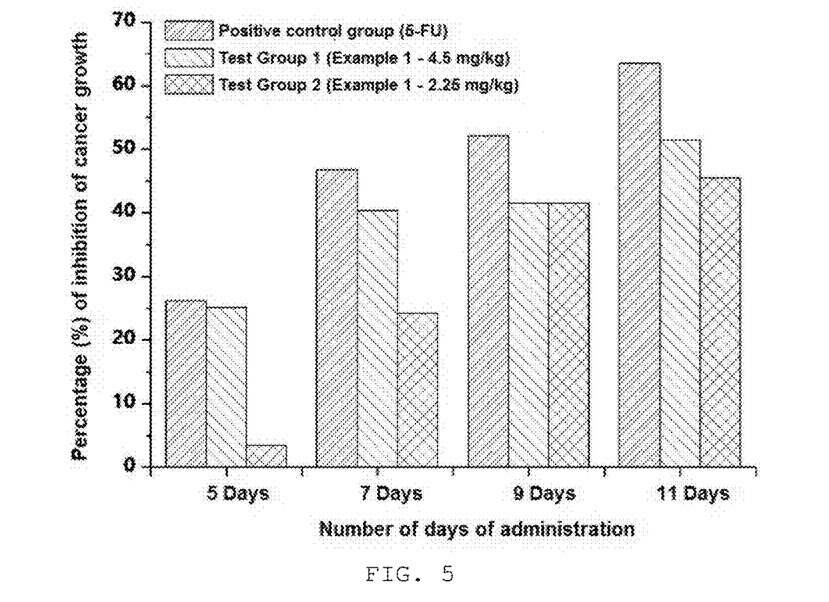
FIG. 5 is a graph showing the results of assessing the percentage of inhibition of cancer growth by observing the changes in cancer volume according to the treatment amount and treatment time of Example 1 when mice transplanted with the human hepatoma cell line H22 cells were treated with Example 1.

In addition, as shown in Table 5 above and FIG. 5, the percentage of inhibition of cancer volume growth was increased according to the period of administration when Example 1 was treated, and the percentage of inhibition of cancer volume growth was higher in Test Group 1 administered with 4.5 mg/kg Example 1 compared with Test Group 2 administered with 2.25 mg/kg Example 1.

It can be seen through these results that Example 1 of the present invention inhibits the growth of liver cancer.

Test Example 3: In Vivo Efficacy Test in Animal Models Transplanted with Human Liver Cancer Cell Line SMMC-7721 Cells (1) Methods Human liver cancer cell line SMMC-7721 cells (purchased from the Shanghai Cell Bank of Chinese Academy of Sciences) were incubated in RPMI-1640 medium supplemented with 10% FBS, 50 U/ml penicillin, and 50 μg/ml streptomycin in an incubator under conditions of 37° C., 5% $CO_2$, and 95% air. The medium was exchanged every three days.

Twenty five 5-week-old babl/c-nu male mice, which were safe from specific pathogens and respiratory diseases and had a body weight of 18-20 g, were used as experimental animals. The mice were allowed free access to food and water, and were bred in a 12-hr light/12-hr dark cycle.

The twenty five mice were subcutaneously inoculated into the neck site with SMMC-7721 cells at $2 \times 10^7$ cells per mouse, and bred for 7 days. On 7 days after the cell inoculation, the mice were randomly divided into 5 mice per group, and then test groups were designated as shown in Table 6 below, and respective corresponding samples were orally administered daily for 7 days. 5-Fluorouracil (5-FU), which is used as an anticancer drug, was treated for a positive control group.

TABLE 6

| Group | Reagent treatment |
|---|---|
| Cancer model group | Distilled water |
| Positive control group | 5-Fluorouracil - 20 mg/kg |
| Test Group 1 | Example 1 - 4.5 mg/kg |
| Test Group 2 | Example 1 - 2.25 mg/kg |
| Test Group 3 | Example 1 - 1.125 mg/kg |

(2) Investigation of Inhibition of Cancer Growth

Cancer tissues were isolated from the mice after seven days of administration of the drug for each group, and visually observed. Cancer weights were measured. In addition, the inhibition of cancer growth was calculated on the basis of the measured weights of the cancer tissues by using the following equation. The results are shown in Table 7 and FIG. 6.

Percentage of inhibition of cancer growth=(1−(sample treatment group/cancer model group))×100

TABLE 7

| Group | Cancer weight (g) | Percentage (%) of inhibition of cancer growth |
|---|---|---|
| Cancer model group | 1.07 ± 0.52 | — |
| Positive control group | 0.72 ± 0.27 | 32.5 |
| Test Group 1 | 0.65 ± 0.17 | 39.7 |
| Test Group 2 | 0.70 ± 0.10 | 34.3 |
| Test Group 3 | 0.77 ± 0.12 | 28.0 |

Figure 6:
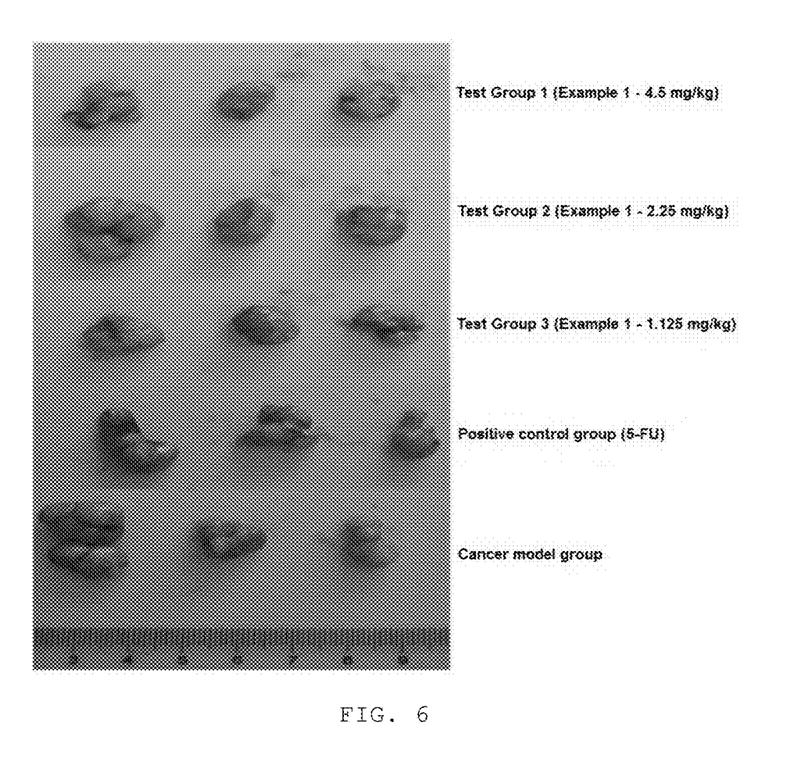
FIG. 6 shows changes in cancer tissue size according to the treatment with Example 1 when mice transplanted with the human hepatoma cell line SMMC-7721 cells were treated with Example 1 of different concentrations.

As can be seen from Table 7 above, it was confirmed that the cancer weight was reduced in Test Groups 1 to 3 administered with Example 1 compared with the cancer model group, and the cancer weight was reduced depending on the dose of Example 1. FIG. 6 also shows that the tumor tissue sizes were reduced according to the administration of Example 1.

It can be seen through these results that Example 1 of the present invention inhibits the growth of liver cancer.

The invention claimed is:

1. A pharmaceutical composition containing tetraarsenic hexoxide ($As_4O_6$) as an active ingredient for treatment of liver cancer, wherein the tetraarsenic hexoxide includes 99 wt % or more of tetraarsenic hexoxide crystalline polymorph (a) having features (i) to (iii) below:
   (i) Cell parameters:
   a=b=c=11.0734 Å
   α=β=γ=90°
   V=1357.82 Å$^3$
   (ii) As—O bond length: 1.786 Å
   (iii) O—As—O bond angle: 98.36°,
   wherein the pharmaceutical composition further comprises at least one of a carrier, a diluent, and an excipient.

2. The pharmaceutical composition of claim 1, wherein the tetraarsenic hexoxide is prepared by:
   a first step of heating sodium chloride at 100~800° C., followed by cooling;
   a second step of placing arsenic trioxide ($As_2O_3$) on the sodium chloride, followed by heating from 100° C. to 1000° C. in an airtight state and then cooling;
   a third step of separating crystals crystallized in a filter bed collecting sublimated arsenic; and
   a fourth step of repeating the second and third steps four to ten times using the crystals obtained in the third step instead of the arsenic trioxide in the second step, thereby obtaining tetraarsenic hexoxide crystals.

3. The pharmaceutical composition of claim 1, wherein the tetraarsenic hexoxide has a purity of 99.9% or higher.

4. The pharmaceutical composition of claim 1, wherein in the X-ray powder diffraction spectrum of the crystalline polymorph a, obtained by using a light source wavelength of 1.5406 Å within a diffraction angle (2θ) of 10° to 50° at a rate of 1°/min (scan step of 0.02°), peaks are shown at 2θ values of 13.84, 27.88, 32.32, 35.3, 39.84, 42.38, 46.34, 48.6, and 49.34.

5. The pharmaceutical composition of claim 1, wherein the carrier, the diluent, or the excipient is at least one of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, propylene glycol, polyethylene glycol, vegetable oils, injectable esters, Witepsol, Macrogol, Tween 61, cacao butter, laurin butter, and glycerogelatin.

\* \* \* \* \*